(12) United States Patent
Tehrani et al.

(10) Patent No.: US 8,312,920 B2
(45) Date of Patent: Nov. 20, 2012

(54) METHOD AND APPARATUS FOR AUTOMATED FLUID LOSS MEASUREMENTS OF DRILLING FLUIDS

(75) Inventors: Mostafa Ahmadi Tehrani, Banchory (GB); Jacqueline Joan Cameron, Aberdeen (GB)

(73) Assignee: M-I L.L.C., Houston, TX (US)

( * ) Notice: Subject to any disclaimer, the term of this patent is extended or adjusted under 35 U.S.C. 154(b) by 348 days.

(21) Appl. No.: 12/599,891

(22) PCT Filed: Apr. 25, 2008

(86) PCT No.: PCT/US2008/061481
§ 371 (c)(1),
(2), (4) Date: Jan. 8, 2010

(87) PCT Pub. No.: WO2008/144165
PCT Pub. Date: Nov. 27, 2008

(65) Prior Publication Data
US 2010/0139914 A1 Jun. 10, 2010

Related U.S. Application Data

(60) Provisional application No. 60/938,831, filed on May 18, 2007.

(51) Int. Cl.
*E21B 21/06* (2006.01)
(52) U.S. Cl. ........................ 166/75.12; 166/267; 175/207
(58) Field of Classification Search .................. 73/61.62, 73/61.63; 166/250.01, 267, 75.12; 175/48, 175/212, 207
See application file for complete search history.

(56) References Cited

U.S. PATENT DOCUMENTS

| | | | |
|---|---|---|---|
| 4,538,452 A * | 9/1985 | Hrvojic | 73/61.64 |
| 4,748,849 A | 6/1988 | Jamison et al. | |
| 5,053,141 A | 10/1991 | Laiho | |
| 5,233,863 A | 8/1993 | Surjaatmadja et al. | |
| 5,309,761 A * | 5/1994 | Ravi et al. | 73/152.21 |
| 5,965,029 A * | 10/1999 | Simon et al. | 210/663 |
| 6,543,276 B2 | 4/2003 | Murphy, Jr. et al. | |
| 2003/0029230 A1 * | 2/2003 | Murphy et al. | 73/61.63 |

OTHER PUBLICATIONS

Examination Report issued in corresponding British Application No. GB0920405.8; Dated Mar. 14, 2011 (2 pages).
International Search Report from PCT/US2008/061481 dated Oct. 16, 2008 (2 pages).

* cited by examiner

*Primary Examiner* — Kenneth L Thompson
*Assistant Examiner* — Catherine Loikith
(74) *Attorney, Agent, or Firm* — Osha Liang LLP

(57) ABSTRACT

A drilling fluid test device including a cell body having a pressurization inlet configured to allow for pressurization of the cell body, a fluid inlet configured to provide a test fluid, a filtrate outlet configured to discharge a filtrate, and a fluid outlet configured to discharge the fluid. The device also including a filter medium disposed in the cell body and a cleaning system disposed in the cell body and configured to clean the filter medium. Additionally, a method of testing a drilling fluid including injecting a drilling fluid into an automated testing cell, the automated testing cell having a filter medium. Furthermore, pressurizing the automated testing cell, forming a filter cake on the filter medium, and separating the drilling fluid into a filtrate and a residual drilling fluid. Additionally, transferring the filtrate to a filtrate collection vessel and determining a volume of filtrate in the filtrate collection vessel.

22 Claims, 4 Drawing Sheets

METHOD AND APPARATUS FOR AUTOMATED FLUID LOSS MEASUREMENTS OF DRILLING FLUIDS

BACKGROUND

1. Field of the Disclosure

The present disclosure generally relates to apparatuses and methods for testing drilling fluids used in subterranean drilling operations. More specifically, the present disclosure relates to apparatus and methods for testing drilling fluids containing fluid loss control agents used in subterranean drilling operations. More specifically still, the present disclosure relates to apparatus and methods for testing drilling fluids containing fluid loss control agents using an automated testing and cleaning device.

2. Background Art

When drilling or completing wells in earth formations, various fluids typically are used in the well for a variety of reasons. The fluid may be either water-based or oil-based. For the purposes herein, such fluid will be referred to as "well fluid." Common uses for well fluids include: lubrication and cooling of drill bit cutting surfaces while drilling generally or drilling-in (i.e., drilling in a targeted petroliferous formation), transportation of "cuttings" (pieces of formation dislodged by the cutting action of the teeth on a drill bit) to the surface, controlling formation fluid pressure to prevent blowouts, maintaining well stability, suspending solids in the well, minimizing fluid loss into and stabilizing the formation through which the well is being drilled, minimizing fluid loss into the formation after the well has been drilled and during completion operations such as, for example, perforating the well, replacing a tool, attaching a screen to the end of the production tubulars, gravel-packing the well, or fracturing the formation in the vicinity of the well, displacing the fluid within the well with another fluid, cleaning the well, testing the well, fluid used for emplacing a packer, abandoning the well or preparing the well for abandonment, and otherwise treating the well or the formation.

A variety of compounds may be added to well fluids to enhance performance. Among these compounds are fluid loss control agents, which act by coating the walls of the wellbore, as the well is drilled, with a thin layer of low-permeability filtercake. The filtercake helps to reduce the amount of base fluid lost to the formation and prevents undesirable variations in the density and rheology of the drilling fluid. Additionally, the filtercake helps prevent formation damage in the reservoir, which may be caused by blockage of formation pores through invasion of wellbore fluid. Filtercake also provides a barrier to prevent the influx and efflux of drilling fluids between the wellbore and the formation. Suitable fluid loss control additives, for both water-based and oil-based drilling fluids include modified starches, synthetic resins, modified lignites, asphaltic compounds, gilsonites, and a wide range of other polymeric and non-toxic fluid loss control materials. Such fluid loss control agents may be generally used in drilling fluids, or may be used in gel pills used to prevent fluid loss in a particular zone of the wellbore.

The role of the fluid loss characteristics of the well fluid demands that the properties of the well fluid are carefully monitored throughout the operation, and that corrective measures are taken in time to maintain required specifications of the fluids in the operation. Fluid loss is conventionally measured by industry standard American Petroleum Institute ("API") tests. The API tests require the use of a new filter for every test. The requirement for a new filter necessitates the dismantling and cleaning of the testing device (i.e., a filtration cell) between successive tests. Additionally, both the low-temperature/low-pressure and the high-temperature/high-temperature tests require manual cleaning of the internal chambers of the filtration cells between subsequent tests. Taking apart the filtration cell, cleaning the internal chamber, and replacing the filter between tests is time consuming, expensive, and require operator attendance through the entire test.

Accordingly, there exists a continuing need for improvements in drilling fluid testing devices.

SUMMARY OF THE DISCLOSURE

In one aspect, embodiments of the present disclosure include a drilling fluid test device including a cell body having a pressurization inlet configured to allow for pressurization of the cell body, a fluid inlet configured to provide a test fluid, a filtrate outlet configured to discharge a filtrate, and a fluid outlet configured to discharge the fluid. The device also including a filter medium disposed in the cell body and a cleaning system disposed in the cell body and configured to clean the filter medium.

In another aspect, embodiments of the present disclosure include a method of testing a drilling fluid including injecting a drilling fluid into an automated testing cell, the automated testing cell having a filter medium. Furthermore, pressurizing the automated testing cell, forming a filter cake on the filter medium, and separating the drilling fluid into a filtrate and a residual drilling fluid. Additionally, transferring the filtrate to a filtrate collection vessel and determining a volume of filtrate in the filtrate collection vessel.

Other aspects and advantages of the disclosure will be apparent from the following description and the appended claims.

DETAILED DESCRIPTION

Generally, embodiments disclosed herein relate to apparatuses and methods for testing drilling fluids used in subterranean drilling operations. More specifically, embodiments disclosed herein relate to apparatuses and methods for testing drilling fluids containing fluid loss control agents used in subterranean drilling operations. More specifically still, embodiments disclosed herein relate to apparatuses and methods for testing drilling fluids containing fluid loss control agents using an automated testing and cleaning device.

Embodiments of the present disclosed may provide for the testing of drilling fluids containing fluid loss control agents typically tested using the devices discussed above. Those of ordinary skill in the art will appreciate that the apparatuses and methods disclosed herein may be used to test both oil-based and water-based drilling fluids containing varied fluid loss control agents, such as, starches, synthetic resins, modified lignites, asphaltic compounds, and gilsonites.

Figure 1A:
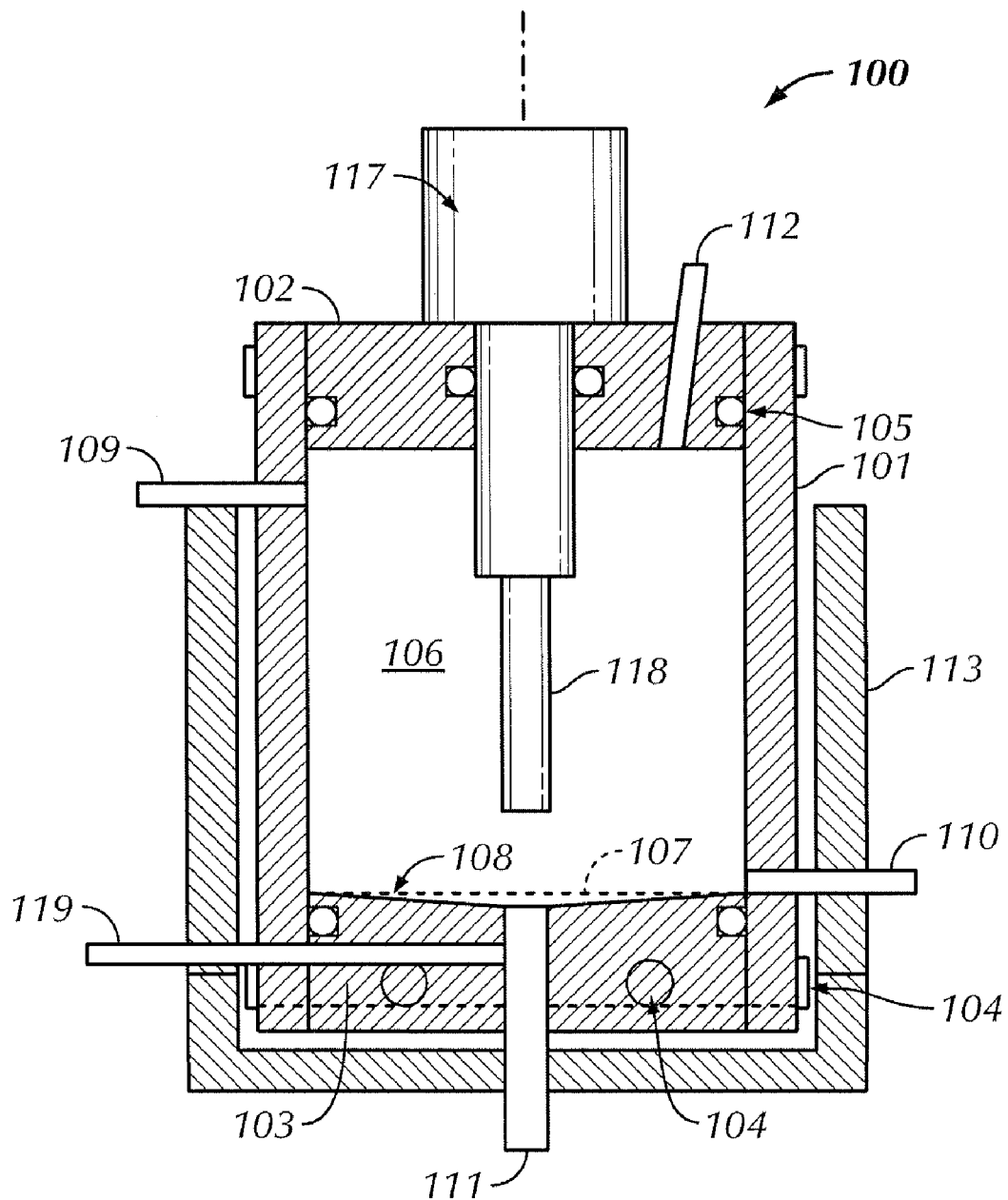
FIG. 1A shows a cross-sectional view of a drilling fluid test device according to embodiments of the present disclosure.

Referring initially to FIG. 1A, a cross-sectional view of a drilling fluid test device 100 according to embodiments of the present disclosure is shown. In this embodiment, drilling fluid test device 100 includes a cell body 101 having a top end plate 102 and a bottom end plate 103. In certain aspects, cell body 101 and end plates 102 and 103 may be formed from stainless steel, such as grade 316 stainless steel. However, those of ordinary skill in the art will appreciate that cell body 101 and end plates 102 and 103 may also be formed from other materials capable of withstanding the pressures and temperatures used in drilling fluid tests. For example, according to API recommended practices, a filtration cell used in conventional drilling fluid high-temperature/high-pressure tests should be able to withstand working pressures of up to 1300 psi. Thus, it may be desirable for drilling fluid test device 100 to be capable of withstanding similar pressures.

In this embodiment, top end plate 102 and bottom end plate 103 are securably attached to cell body 101. End plates 102 and 103 may be attached to cell body 101 using, for example, screws (104), rivets (not shown), or other mechanical fasteners. In other aspects, one or more of end plates 102 and 103 may be removably attached to cell body 101 using hinges (not shown), retainer bars (not shown), or other means of removably attaching components known in the art. Those of ordinary skill in the art will appreciate that the specific type of attachment is not a limitation on the scope of the present disclosure. However, embodiments disclosed herein may include attachment of end plates 102 and 103 to cell body 101 such that a sealing engagement is formed. As such, drilling fluids injected into cell body 101 may only be discharged from the system through specified outlets. To prevent the discharge of drilling fluids through interface surfaces of endplates 102 and 103 and cell body 101, a plurality of seals 105 may be disposed between the components. Seals 105 may be formed from, for example, rubbers and/or elastomers. Those of ordinary skill in the art will appreciate that in alternate embodiments, cell body 101 may be formed such that only one end plate, for example either a top end plate 102 or a bottom end plate 103, is required. In such an embodiment, the one end plate may be securably attached to the cell body 101, according to the methods described above.

A filter medium 107 may be disposed inside an inner chamber 106 of drilling fluid test device 100. Filter medium 107 may include any type of filter medium used to test drilling fluids including perforated ceramic plates, polycarbonates, metallic surface filters, and fibrous filters. Those of ordinary skill in the art will appreciate that filter medium 107 used with embodiments disclosed herein may be configured to be disposed in an impinging-flow drilling fluid testing device, such as device 100. Impinging-flow, also known in the art as deadend flow, refers to a fluid that flows perpendicular to a surface (as opposed to surface-flow, which describes the flow of a fluid parallel to a surface). According to embodiments of the present disclosure, filter medium 107 may be used in a drilling fluid testing device such that a flow of fluid is perpendicular to the arrangement of filter medium 107 within device 100, as illustrated in FIG. 1.

Those of ordinary skill in the art will appreciate that the filter medium may generally consist of a thin sheet of material with narrow slots through which a filtrate may pass. Depending on the specific drilling fluid and/or drilling fluid loss control agent being tested, the size of the perforations may vary. For example, in some embodiments, the width of the perforations may range from 2 microns to 20 microns. In other embodiments, the width of the perforations may range between 5 and 8 microns. In one aspect, filter medium 107 may include a reusable medium capable of being cleaned within drilling fluid test device 100 between testing operations. Examples of reusable medium include the medium disclosed in co-pending U.S. Provisional application Ser. No. 60/938,825, assigned to the assignee of the present disclosure, and hereby incorporated by reference in its entirety. Those of ordinary skill in the art will appreciate that in certain embodiments, filter medium 107 may include a plurality of filter media or layers of filtering elements. As such, filter medium 107 is germane to any configuration of filtering elements, including one or a plurality of filtering elements, known to those of ordinary skill in the art.

Figure 1B:
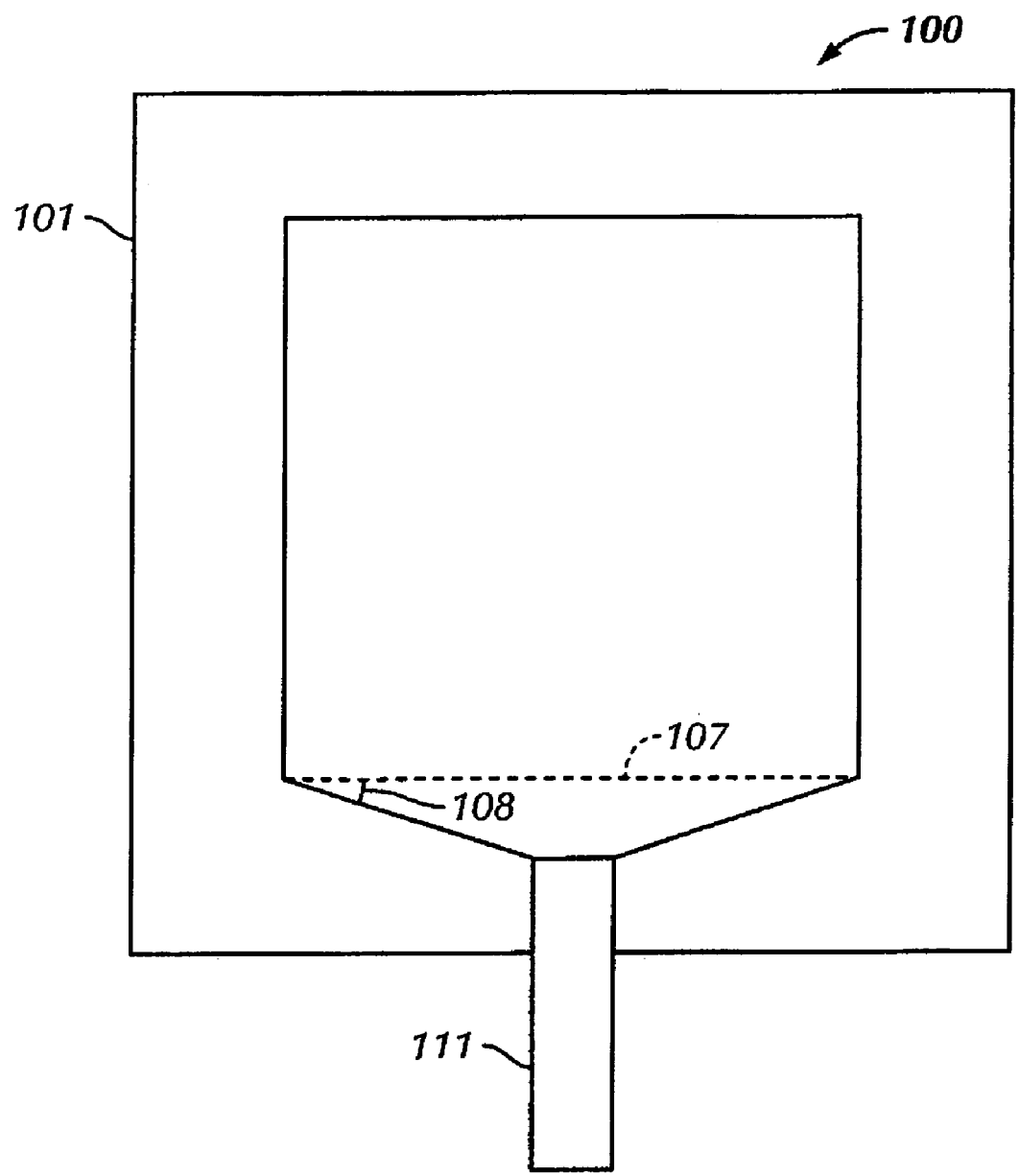
FIG. 1B shows a cross-sectional view of a drilling fluid test device according to embodiments of the present disclosure.

Referring briefly to FIG. 1B, a cross-sectional view of drilling fluid test device 100 is shown. In this embodiment, filter medium 107 may be disposed substantially perpendicular to cell body 101. In such an embodiment, bottom end plate 103 may include a radial slope 108 along an inner surface to assist in the discharge of filtrate from cell body 101. The degree of radial slope is not a limitation on the scope of the present disclosure, and may be varied according to the types and/or viscosity of the drilling fluid being tested. As such, in certain aspects, radial slope 108 may range between 0° and 45°, while in alternate aspects, radial slope 108 may range between 5° and 15°. Those of ordinary skill in the art will appreciate that in certain embodiments, radial slope 108 may not be necessary, and filtrate may discharge from cell body 101 without such assistance.

Referring back to FIG. 1A, test drilling fluid may be injected into cell body 101 via a fluid inlet 109. As illustrated, fluid inlet 109 is located proximate top end cap 102, substantially closer to top end cap 102 than filter medium 107. As such, a volume of drilling fluid injected into cell body 101 may not be limited by the placement of fluid inlet 109. However, in alternate embodiments, it may be beneficial for fluid inlet 109 to be disposed in closer proximity to filter medium 107, and as such, the precise location of fluid inlet 109 is not meant as a limitation on the scope of the present disclosure. Generally, fluid inlet 109 is configured to provide the test drilling fluid to cell body 101, and as such, fluid inlet 109 may be in fluid communication with a drilling fluid storage reservoir (not shown) and a plurality of valves (not shown) for controlling the flow of the drilling fluid therethrough.

Cell body 101 also includes a fluid outlet 110 that is configured to allow for the discharge of residual drilling fluid from cell body 101. As illustrated, fluid outlet 110 is disposed proximate bottom end cap 103 above filter medium 107. While in this embodiment fluid outlet 110 is disposed directly above filter medium 107, in alternate embodiments, fluid outlet 110 may overlap with the profile of filter medium 107, or otherwise be located closer to top end cap 102 than filter medium 107. However, the closer in proximity fluid outlet 110 is disposed relative to filter medium 107, the more effective cleaning operations may be. Fluid outlet 110 may be in fluid communication with a discharge reservoir (not illustrated), pumps (not shown), or other components used to help discharge and/or clean residual drilling fluids from cell body 101. In one embodiment, fluid outlet 110 may be configured to interface with a vacuum device such that residual fluid is vacuumed out of cell body 101. In alternate embodiments, low pressure gas may be injected into cell body 101 to facilitate the flow of residual drilling fluid out of fluid outlet 110. In still other embodiments, a washing fluid may be injected into cell body 101, and may subsequently be transferred out of fluid outlet 110 via pumping, suction, or applied pressures, as described above.

Embodiments of cell body 101 also include a filtrate outlet 111 configured to receive a discharge flow of filtrate from cell body 101. Generally, filtrate outlet 111 may be disposed as a conduit through bottom end plate 103, thereby providing fluid communication between cell body 101 and downstream processing and/or collection components. In this embodiment, filtrate outlet 111 is located below filter medium 107 such that as filtrate passes through filter medium 107 the filtrate may be discharged from cell body 101. As illustrated, the flow of filtrate through filtrate outlet 111 may be assisted by radial slope 108. As such, in certain embodiments, filtrate outlet 111 may be configured along a recessed portion of bottom end plate 103. Additionally, in alternate embodiments, filtrate outlet 111 may be disposed along any portion of cell body 101 below filter media 107, so as to receive a flow of filtrate passing therethrough. Thus, in certain aspects, filtrate outlet 111 may be disposed as a conduit through bottom end cap 103, cell body 101, or through another components of drilling fluid test device 100.

Cell body 101 also includes a pressurization inlet 112 configured to allow for the pressurization of cell body 101. Pressurization inlet 112 may be disposed anywhere on cell body 101 such that a supply of air (e.g., oxygen-free nitrogen and other inert gases) may be pumped into cell body 101 to provide a positive pressure to a fluid contained therein. As illustrated, pressurization inlet 112 may be disposed as a conduit through top end cap 102, and may be in fluid communication with an air compression device capable of providing a pressurization gas to cell body 101. In certain embodiments, pressurization inlet 112 may be in fluid communication with additional components such as, for example, remote-controlled pressure regulator valves (not shown) that may be used to adjust the pressure of a gas. Exemplary pressures may include providing gas between 100 and 600 psi. Additional components may include pressure gauges (not shown), relief valves (not shown), and other components used during pressurization of testing cells known to those of ordinary skill in the art.

Figure 2:
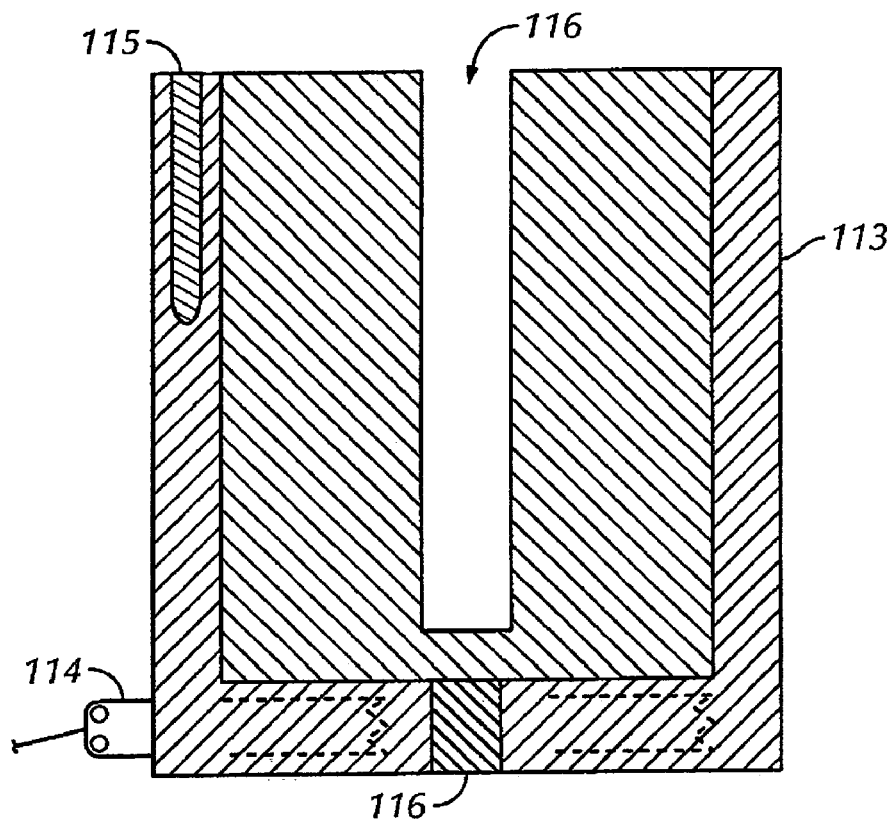
FIG. 2 shows a side cross-sectional view of a drilling fluid test device according to embodiments of the present disclosure.
Figure 3:
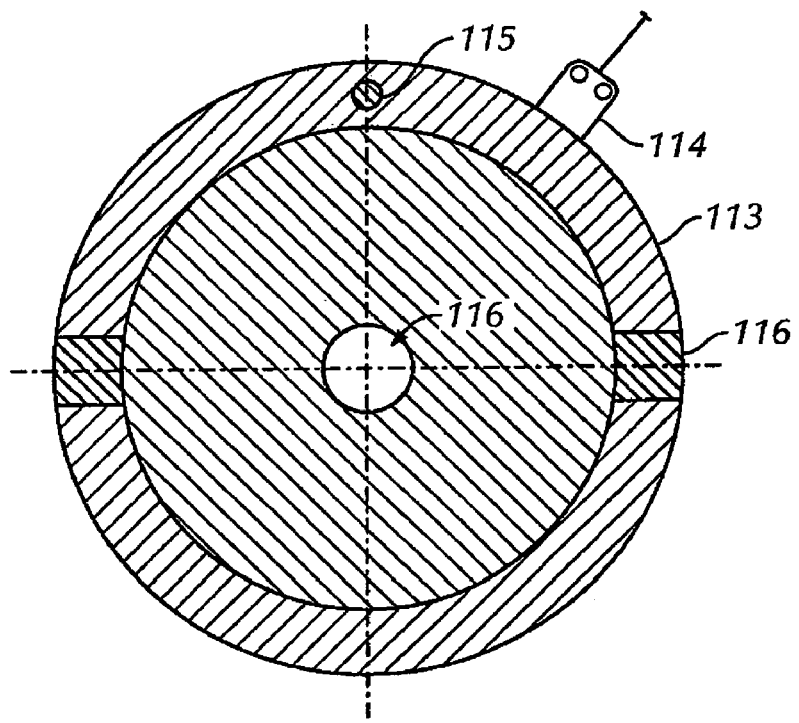
FIG. 3 shows a top cross-sectional view of a drilling fluid test device according to embodiments of the present disclosure.

In certain embodiments, a heating jacket 113 may be disposed around cell body 101 and/or end caps 102 and 103. Referring briefly to FIGS. 2 and 3, side and top cross-sectional views of drilling fluid test device 100 according to embodiments of the present disclosure are shown. Heating jacket 113 may include a heating element 114 disposed or formed integral to heating jacket 113. Heating element 114 may be configured to a control system (not shown) such that a temperature level of heating jacket 113 may be controlled. The temperature of heating jacket 113 may be determined via a thermocouple 115 disposed in heating jacket 113. Additionally, heating jacket 113 may include a plurality of slits/conduits 116 to accommodate components of the cell body (101 of FIG. 1A). For example, slits/conduits 116 in heating jacket 113 may accommodate any of the inlets and/or outlets described above.

Referring back to FIG. 1A, embodiments of the present disclosure may also include a cleaning system disposed in cell body 101 configured to clean filter medium 107. In this embodiment, the cleaning system includes an ultrasonifier probe 117. Upon actuation, ultrasonifier probe 117 may provide sonic waves to components of drilling fluid test device 100, such as filter medium 107, or the internal walls (not independently illustrated) of cell body 101 and end caps 102 and 103. The sonic waves may facilitate the breaking-up and dispersal of solids adhered to internal components of drilling fluid test device 100 during testing. For example, the sonic waves generated by ultrasonifier probe 117 may assist in breaking-up a filtercake that forms on filter medium 107.

Additionally, during testing, residual fluid in cell body 101 may leave solids deposits along inlets, outlets, or along inner walls of any of the components discussed above. Those of ordinary skill in the art will appreciate that the location of ultrasonifier probe 117 may vary depending on the type of probe used and the specific geometry of drilling fluid test device 101. However, in one embodiment, a gap should be left between a tip 118 of ultrasonifier probe 117 and filter medium 107 to provide the greatest cleaning efficiency.

For example, if the dimensions of the drilling fluid test device include an internal diameter of 2.1 inches and a height of 6.0 inches, a 0.5 inch diameter probe may be disposed between 1.0 and 2.5 inches from filter media 107. However, in certain embodiments it may be preferable for the gap to range between 1.5 and 2.0 inches. Those of ordinary skill in the art will appreciate that the gap between tip 118 and filter medium 107 may vary in accordance with design variations of drilling fluid test device 100. As such, the precise location of ultrasonifier probe 117 within cell body 101 is not a limitation on the scope of the present disclosure.

In certain embodiments, the cleaning system of drilling fluid test device 100 may require a washing fluid inlet 119 disposed in cell body 101 and/or bottom end cap 103. Washing fluid inlet 119 is configured to provide washing fluid to filter medium 107 and/or filtrate outlet 111. Exemplary washing fluids may include water, base oil, brine solution, or solutions including surfactants to facilitate the removal of solids from the internal components of drilling fluid test device 100. Generally, a washing fluid may be injected through washing fluid inlet 119 via an injection pump (not shown). The washing fluid may assist in cleaning the internal components, and may also provide a back-flush of fluid to filter medium 107. The back-flush may assist in breaking-up a filtercake formed on or in perforations of filter medium 107. Those of ordinary skill in the art will appreciate that in certain embodiments, washing fluid inlet 119 may be disposed along any portion of drilling fluid test device 100, and may be used to inject the washing fluid directly into internal chamber 106. In such an embodiment, washing fluid inlet 119 may alternatively be disposed above filter medium 107.

Those of ordinary skill in the art will appreciate that additional components may be configured to interface or communicate with the components of drilling fluid test device 100 discussed above. While not illustrated independently, additional components may include a plurality of pumps and valves to control the flow of test fluids through drilling fluid test device 100. In other embodiments, a condenser (not shown) may be disposed to receive a flow of filtrate from filtrate outlet 111. Moreover, in certain embodiments a central control unit (not shown) may be configured to provide instructions to drilling fluid test device 100. Examples of central control units may include programmable logic controllers ("PLC") disposed proximate and in communication with drilling fluid test device 100 to record measurements or provide instructions to components of the device. Alternate central control units may include computers, such as, for example, personal and/or laptop computers capable of running software to provide instructions to components of drilling fluid test device 100.

In one embodiment, central control units may provide instructions for the actuation of valves or pumps to provide drilling fluids, washing fluids, and gases (used in pressurization). Additionally, central control units may provide instructions that control automated testing and/or cleaning operations, as will be discussed in greater detail below. In still other embodiments central control units may receive data from components of drilling fluid test device 100, such as images, temperature measurements, and volumetric measurements, and may subsequently process such data.

Examples of data processing may include determining volumes of filtrate, drilling fluids, injected gases, pressures, temperatures, flow rates, and other variable known to those of ordinary skill in the art. In one embodiment, the central control unit may be configured to receive filtrate data from a measurement device (e.g., a digital camera, a load cell, or level sensors). In one aspects, an imaging device may collect filtrate data in the form of visual representations of aspects of the testing operation. Exemplary visual representations may include photographs of filtrate in a filtrate collection vessel. The filtrate data may then be processed by the central control unit using software to determine a volume of filtrate in the filtrate collection vessel. The processed filtrate data may then be output by the central control unit as a visual representation, numerical data, printed data, or in the formulation of additional instructions for controlling an operation of drilling fluid test device 100. Furthermore, the output may control testing and/or cleaning operations, as will be described below. In other embodiments, the measurement device may include load cells for collecting weight data or level sensors or determine the amount of filtrate in a the filtrate collection vessel.

Those of ordinary skill in the art will appreciate that specific components of drilling fluid test device 100 may not be necessary, and as such, the scope of the present disclosure should only be limited by the appended claims.

Figure 4:
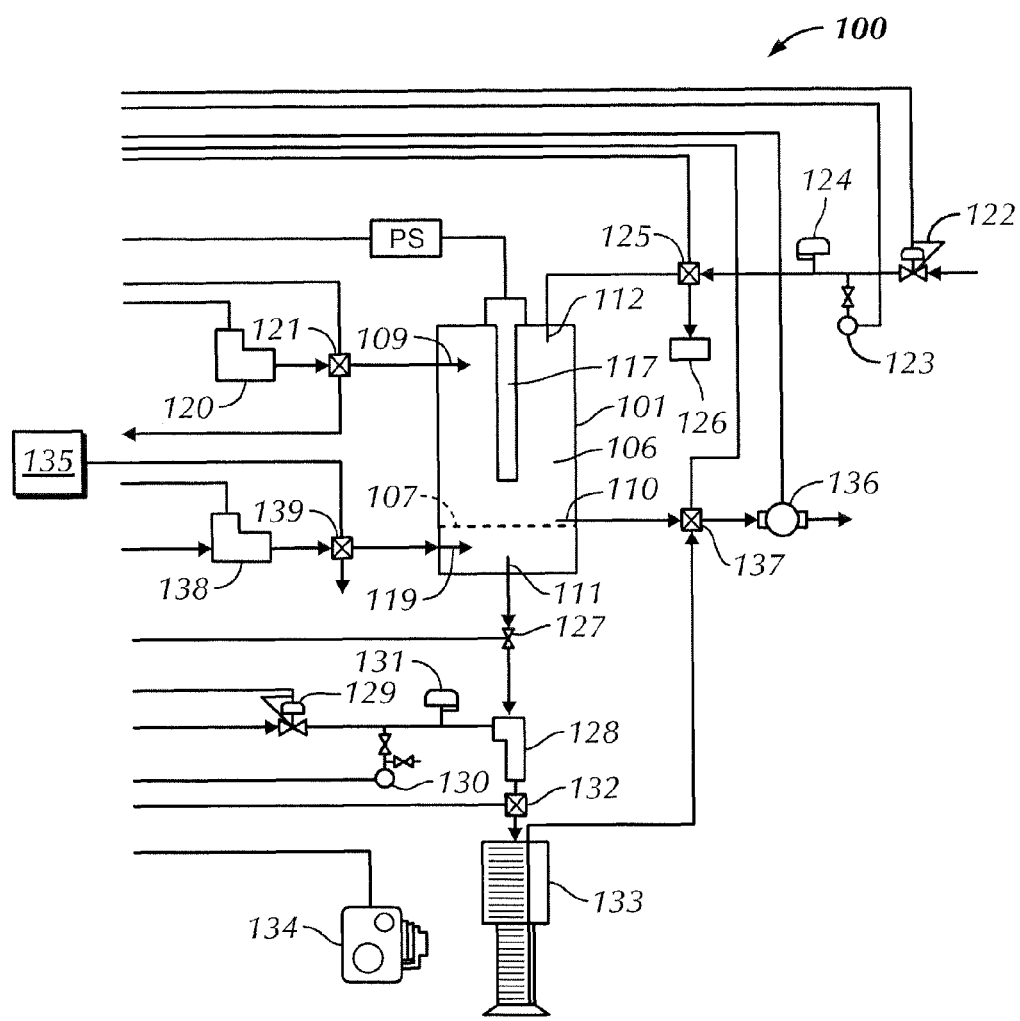
FIG. 4 shows a schematic of a drilling fluid test device according to embodiments of the present disclosure.

Referring to FIG. 4, an operational schematic of a drilling fluid test device 100 according to embodiments of the present disclosure is shown. In the operational schematic, like numbers from FIG. 1A-3 represent like components. Thus, individual components of FIG. 4 may include like properties of the components discussed above.

Initially, a test fluid is injected into the drilling fluid test device via a test fluid injection pump 120. The test fluid may have been previously stored in a storage vessel (not shown) in fluid communication with injection pump 120. In one embodiment, injection pump 120 may be a syringe-type or metering pump. However, generally, injection pump 120 may be any pump capable of injecting a specified volume of drilling fluid. Once the test fluid is injected, drilling fluid test device 100 is isolated from injection pump 120 by, for example, a remote-controlled three-way valve 121. Those of ordinary skill in the art will appreciate that injection pump 120 and valve 121 may be preferably operable in bypass mode to prevent gellation of test fluid lines connecting the components.

Once a known volume of test fluid is injected into the drilling fluid test device 100, a gas is used to pressurize internal chamber 106 of the drilling fluid test device. A remote-controlled pressure regulator valve 122 may be used to adjust the gas pressure, such that a preferable pressure range is achieved. Those of ordinary skill in the art will appreciate that in certain embodiments, it may be preferable to test the drilling fluid in an environment between 100 and 600 psi, however, in alternate embodiments, the pressure may range between 0 and 1300 psi. The pressure may be measured by a pressure gauge 123, while a relief valve 124 may be included to prevent an incidental pressure build-up. A remote-controlled three-way valve 125 may be used to regulate the injection of gas to pressurization inlet 112. Additionally, during cleaning stages, valve 125 may be used to de-pressurize the drilling fluid test device 100 by releasing gas from vent 126.

During operation of the drilling fluid test device 100, the drilling fluid separates into a filtrate and a residual fluid, as the perforations of filter medium 107 become plugged with fluid loss control agents. Filtrate that passes through filter medium 107 may exit the drilling fluid test device via filtrate outlet 111. In this embodiment, filtrate passes through a remote-controlled valve 127 before entering a condenser 128. Condenser 128 provides back pressure and cools the filtrate during filtration, while valve 127 may be used to control a flow of filtrate through filtrate outlet 111 during both testing and cleaning phases of operation. Back pressure may be provided by the injection of gas into condenser 128, and the regulation of such gas injection may be controlled by, for example, a pressure regulator valve 129, a pressure gauge 130 and a relief valve 131, as discussed above. The filtrate accumulated in condenser 128 may then be released through a valve 132 fluidly connecting condenser 128 to a filtrate collection vessel 133. In one embodiment filtrate collection vessel 133 may include a graduated cylinder having two different cross-sectional areas, thereby allowing for the collection and measuring of both low fluid loss and high fluid loss fluids. At the end of the testing phase, after the filtrate has exited the drilling fluid test device into filtrate collection vessel 133, a remote-operated imaging device 134 records an image of filtrate collection vessel 133 and the filtrate disposed therein. The image is then conveyed to a central control unit 135 for analysis, as described above. After the measurements are complete, the filtrate may be discharged from filtrate collection vessel 133 via a vacuum pump 136, and discarded and/or recycled accordingly.

Generally, after the testing phase is complete, the drilling fluid test device 100 is allowed to cool and is de-pressurized by gradually opening valve 125 to allow gas in internal chamber 106 exit via vent 126. The test fluid may then be discharged from the drilling fluid test device 100 via actuation of valve 137 connected to vacuum pump 136. Thus, residual drilling fluid may be vacuumed from the drilling fluid test device 100 and discarded and/or recycled accordingly.

After the testing phase, a substantial portion of the residual drilling fluid may have been removed from the drilling fluid test device and the filtrate may also have been removed from filtrate collection vessel 133. However, the filtercake that formed on filter medium 107 during the testing may not have been removed during the discharging of the residual drilling fluid. As such, before another testing phase may begin, the filtercake must be substantially removed from filter medium 107. Furthermore, those of ordinary skill in the art will appreciate that it may be beneficial to clean portions of the filtrate collection vessel 133, internal chamber 106, and/or other internal components of the drilling fluid test device 100.

Generally, cleaning of the filter medium 107 and internal chamber 106 occurs via back-flush washing and ultrasound. A washing fluid may be injected by a constant-pressure pump 138 into a washing fluid inlet 119. The rate of washing fluid injection may vary according to the design of the drilling fluid test device, however, in certain embodiments, it may be beneficial for the flow of washing fluid to range between 50 and 100 mL per minute. Additionally, it may be beneficial to inject sufficient washing fluid to submerge at least a portion of ultrasonifier probe 117. During the testing phase, pump 138 may be isolated from the drilling fluid test device via a valve 139. The pressure of the back-flush from the washing fluid may then lift the filtercake off of filter medium 107, and together with sonification from ultrasonifier probe 117, break-up the filtercake into fine particles dispersed in the back-flush fluid. The level of fluid in internal chamber 106 may be regulated by intermittently switching on vacuum pump 136, thereby allowing the fine particles to exit the drilling fluid test device 100. Substantially all residual fluid and broken-up filtercake may thus be removed from the drilling fluid test device by vacuum and/or low-pressure gas injection. In one aspect, low-pressure gas injection may include the injection of gas at 10-20 psi for several seconds (e.g., 5-10 seconds per component) to remove substantially all fluid from inlets, outlets, and other components of the drilling fluid test device 100.

Those of ordinary skill in the art will appreciate that the remote-controlled device, along with additional components of the drilling fluid test device 100, may be controlled using central control unit 135. As such, central control unit 135 may be programmed to run a testing phase and a cleaning phase while also analyzing data collected during the testing phase and generating an output displaying such results. In certain embodiments, central control unit 135 may generate fluid loss data that includes, for example, fluid loss rates, fluid loss volumes, fluid loss time variables, temperature data, pressure data, and other variables that effect fluid loss known to those of ordinary skill in the art.

To calculate fluid loss, and fluid loss variables, a plurality of images may be recorded during the testing phase of the drilling fluid test device. In one embodiment, images may be recorded at predetermined time intervals during the testing phase, such that a collected filtrate volume may be determined as a function of time. In such an embodiment, images may be collected, for example, every 10 seconds, 30 seconds, or every minute, such that a volume of filtrate collected in the filtrate collection vessel, at regular intervals, may be determined. Those of ordinary skill in the art will appreciate that it may be beneficial to collect images at more frequent intervals early in the testing phase because the flow of filtrate may be higher before the fluid loss control agents form a filtercake along the filter medium. Thus, in one embodiment, images may be taken in 10 second intervals initially, then the time interval increased over time, such that after 5 minutes, images are only taken every minute. The precise time intervals may vary according to the perforation size of the filter media, the type and size of fluid loss control agents being tested, and other specific properties of the drilling fluid test device.

After the collection of the time-tagged images, software in the central control unit may be used to analyze the images, and by identifying the location of filtrate/air interface in the filtrate collection vessel, produce data representative of filtrate volume as a function of time. With such data, an effectiveness of a fluid loss control agent in certain conditions (e.g., pressure and temperature) may be determined. Additionally, by varying a perforation size in the filter media, an effectiveness of a fluid loss control agent for a formation with a known permeability may be determined. Those of ordinary skill in the art will appreciate that the data produced by the central control unit may be output as a visual representation, a numerical representation, or combinations thereof. Furthermore, in certain embodiments, the central control unit may merely collect data from the drilling fluid test device, and components thereof, and store the data for analysis by a remote device. Thus, in certain embodiments, the central control unit may not determine and/or analyze the data, but rather transfer the data to an offsite location for further analysis. Transfer of the data may be through any means for sending data known in the art including, for example, via wireless communication, networks, and/or modems. Furthermore, in certain embodiments, the data may be stored locally for manual review by a drilling engineer.

Advantageously, embodiments of the present disclosure may provide for a testing device for testing drilling fluids and drilling fluid loss control agents that is substantially automated. As such, the drilling fluid test device may be able to implement a testing phase, a cleaning phase, and an analysis phase, and determine properties of drilling fluids and drilling fluid loss control agents. Because the system is substantially automated, the labor required for testing drilling fluids may be decreased, thereby saving money, and allowing for multiple tests to occur contemporaneously.

Also advantageously, embodiments of the present disclosure may provide for a filter medium to be cleaned after a testing phase without dissembling the drilling fluid test device. Because the drilling fluid test device may not require disassembly, cleaning, and reassembly, the time between tests may be decreased, thus increasing the efficiency of testing drilling fluid loss control agents. Further, because the filter media may be reused for multiple tests, the cost of testing fluid loss control agents may be further decreased.

Finally, embodiments of the present disclosure may provide for the automated analysis of drilling fluid such that the efficiency of specific fluid loss control agents may be analyzed. Because the drilling fluid test device allows for the automated collection of time sequenced image data, a fluid loss rate as a function of time for specific fluid loss control agents may be determined. Such determinations may result in more efficient use of fluid loss control agents in drilling operations, thereby decreasing the costs associated with drilling fluids during drilling operating.

While the present disclosure has been described with respect to a limited number of embodiments, those skilled in the art, having benefit of this disclosure, will appreciate that other embodiments may be devised which do not depart from the scope of the present disclosure described herein. Accordingly, the scope of the present disclosure should be limited only by the attached claims.

What is claimed is:

1. A drilling fluid test device comprising:
    a cell body comprising:
        a pressurization inlet configured to allow for pressurization of the cell body;
        a fluid inlet configured to provide a test fluid;
        a filtrate outlet configured to discharge a filtrate;
        a fluid outlet configured to discharge the fluid; and
        a washing fluid inlet configured to provide a washing fluid to a filter medium;
    the filter medium disposed in the cell body; and
    a cleaning system disposed in the cell body and configured to clean the filter medium.

2. The drilling fluid test device of claim 1, wherein the cleaning system comprises:
    an ultrasonifier probe configured to provide sonic waves to the filter medium.

3. The drilling fluid test device of claim 1, further comprising:
    a heating jacket disposed around the cell body.

4. The drilling fluid test device of claim 3, wherein the heating jacket further comprises:
    a heating element.

5. The drilling fluid test device of claim 3, further comprising:
    a thermocouple configured to determine a temperature of the heating jacket.

6. The drilling fluid test device of claim 1, wherein the cell body further comprises a bottom end plate comprising a radial slope.

7. The drilling fluid test device of claim 1, wherein the cell body further comprises:
    a top end plate;
    a bottom end plate; and
    a plurality of seals disposed between the end plates and the cell body.

8. The drilling fluid test device of claim 1, further comprising:
a central control unit configured to provide instructions to the drilling fluid test device.

9. The drilling fluid test device of claim 1, further comprising:
a condenser configured to receive the filtrate from the filtrate outlet.

10. The drilling fluid test device of claim 9, further comprising:
a filtrate collection vessel configured to receive the filtrate from the condenser.

11. The drilling fluid test device of claim 10, further comprising:
a measurement device configured to provide filtrate data to a central control unit.

12. A method of testing a drilling fluid comprising:
injecting a drilling fluid into an automated testing cell, the automated testing cell having a filter medium;
pressurizing the automated testing cell;
forming a filter cake on the filter medium;
separating the drilling fluid into a filtrate and a residual drilling fluid;
transferring the filtrate to a filtrate collection vessel;
determining a volume of filtrate in the filtrate collection vessel; and
running a cleaning cycle on the automated testing cell.

13. The method of claim 12, further comprising:
increasing the temperature in the automated testing cell.

14. The method of claim 12, further comprising:
recording an image of the filtrate in the filtrate collection vessel.

15. The method of claim 14, further comprising:
providing the image of the filtrate to a central control unit; and
analyzing the image with the central control unit to at least determine a volume of the filtrate.

16. The method of claim 12, wherein at least one of the injecting and pressurizing is controlled by a central control unit.

17. The method of claim 12, wherein the cleaning cycle comprises:
providing sonic waves to the filter medium to break up the filtercake.

18. The method of claim 17, wherein the cleaning cycle further comprises:
washing the filter medium with a washing fluid.

19. The method of claim 18, wherein the cleaning cycle further comprises:
discharging the residual drilling fluid from the automated testing cell.

20. The method of claim 18, wherein the cleaning cycle further comprises:
discharging the filtercake from the automated testing cell.

21. The method of claim 20, wherein the cleaning cycle further comprises:
discharging the filtrate from the filtrate collection vessel.

22. A method of testing a drilling fluid comprising:
injecting a drilling fluid into the drilling fluid test device of claim 1.

* * * * *